United States Patent
Kartoun et al.

(10) Patent No.: US 11,694,801 B2
(45) Date of Patent: Jul. 4, 2023

(54) IDENTIFYING AND EXTRACTING STIMULUS-RESPONSE VARIABLES FROM ELECTRONIC HEALTH RECORDS

(71) Applicant: International Business Machines Corporation, Armonk, NY (US)

(72) Inventors: Uri Kartoun, Cambridge, MA (US); Kenney Ng, Arlington, MA (US); Amy Chiu, San Francisco, CA (US); Michael J. Lascaleia, Sudbury, MA (US); Yoonyoung Park, Cambridge, MA (US); Melissa Honour, Westport, CT (US); Amar Das, Cambridge, MA (US); Paul C. Tang, Los Altos, CA (US)

(73) Assignee: International Business Machines Corporation, Armonk, NY (US)

( * ) Notice: Subject to any disclaimer, the term of this patent is extended or adjusted under 35 U.S.C. 154(b) by 315 days.

(21) Appl. No.: 15/979,530

(22) Filed: May 15, 2018

(65) Prior Publication Data
US 2019/0355470 A1 Nov. 21, 2019

(51) Int. Cl.
*G16H 50/20* (2018.01)
*G16H 10/60* (2018.01)
(Continued)

(52) U.S. Cl.
CPC ............ *G16H 50/20* (2018.01); *G06N 20/00* (2019.01); *G16H 10/60* (2018.01); *G16H 10/40* (2018.01)

(58) Field of Classification Search
CPC ........ G16H 50/20; G16H 10/60; G16H 40/20; G16H 40/63; G16H 80/00; G16H 40/67; G16H 10/20; G16H 50/70; G06F 19/30; G06F 19/32; G06F 19/34; G06F 19/36; G06F 3/0484; G06Q 50/22; G06Q 50/24; A61B 5/00; A61B 5/145; A61B 5/168; A61B 5/1118; A61B 5/4815; A61B 5/165; H04L 29/08; H04L 12/24; A01K 1/12;
(Continued)

(56) References Cited

U.S. PATENT DOCUMENTS

2004/0059714 A1* 3/2004 Larsen ........... G06Q 10/063116
2006/0281977 A1 12/2006 Soppet
(Continued)

OTHER PUBLICATIONS

Huang, et al., A methodology for exploring biomarker—phenotype associations: application to flow cytometry data and systemic sclerosis clinical manifestations, Sep. 15, 2015, BMC Bioinformatics (Year: 2015).*

(Continued)

*Primary Examiner* — Michael Tomaszewski
*Assistant Examiner* — Shyam M Goswami
(74) *Attorney, Agent, or Firm* — Patterson + Sheridan, LLP

(57) ABSTRACT

A plurality of events are extracted from a plurality of electronic health records associated with a first patient. The extracted plurality of events are analyzed to identify a plurality of stimulus events and a plurality of response events. An association between a first stimulus event and a first response event is determined. A stimulus-response (SR) variable is generated for the first patient based at least in part on the determined association, and the generated SR variable is integrated into one or more predictive cognitive models.

17 Claims, 5 Drawing Sheets

(51) Int. Cl.
*G06N 20/00* (2019.01)
*G16H 10/40* (2018.01)

(58) Field of Classification Search
CPC .. A01J 5/017; A01J 5/003; B25J 9/144; B25J 9/123; B25J 9/046; B25J 19/0012; B25J 9/1633; B25J 19/0016; G05B 2219/45113; Y10S 901/02
See application file for complete search history.

(56) References Cited

U.S. PATENT DOCUMENTS

| | | |
|---|---|---|
| 2007/0027636 A1 | 2/2007 | Rabinowitz |
| 2008/0228735 A1 | 9/2008 | Kenedy et al. |
| 2011/0251243 A1 | 10/2011 | Tucker et al. |
| 2013/0085773 A1 | 4/2013 | Yao et al. |
| 2013/0085980 A1 | 4/2013 | Alemi |
| 2015/0193583 A1* | 7/2015 | McNair ............... G16H 50/20 705/2 |
| 2015/0310574 A1 | 10/2015 | Williams et al. |
| 2015/0356275 A1* | 12/2015 | Williams ............. G16H 70/20 705/2 |
| 2016/0125137 A1 | 5/2016 | Ott |
| 2017/0249434 A1* | 8/2017 | Brunner ............. G06F 16/3334 |
| 2019/0295718 A1* | 9/2019 | Lawhorn .............. G16H 20/40 |
| 2019/0318818 A1* | 10/2019 | Chaudhuri ........... G16H 10/60 |

OTHER PUBLICATIONS

Smith R.B. (2011) Gauging Causality in Multilevel Models. In: Multilevel Modeling of Social Problems. Springer, Dordrecht, 4 pages. [Abstract Only].

Rima Rudd, "Literacy and Health in America," Educational Testing Service, 2004, 52 pages.

* cited by examiner

IDENTIFYING AND EXTRACTING STIMULUS-RESPONSE VARIABLES FROM ELECTRONIC HEALTH RECORDS

BACKGROUND

The present disclosure relates to predicting outcomes of treatment plans, and more specifically, to identifying, extracting, and using new covariates from data records by utilizing cognitive models Variables or covariates extracted from patient healthcare data can sometimes serve as useful predictors for patient outcomes with various treatment plans. For example, variables representing attributes such as smoking status, alcohol use, and the like have proven indicative of how likely a particular treatment is to be successful in mitigating or controlling medical disorders. Current methods identify a relatively limited and rigid set of variables that may help predict outcomes. These include structured variables (such as comorbidities, medications, laboratory measurements, and the like), as well as unstructured variables extracted from clinical narrative notes. Existing methodologies do not identify or provide methods of acquiring a wider range of more advanced covariates that may achieve increased performance in predicting patient outcomes and enhance performance of even the most sophisticated machine learning algorithms.

SUMMARY

According to one embodiment of the present disclosure, a method is disclosed. The method comprises extracting a plurality of events from a plurality of electronic health records associated with a first patient. The method also includes analyzing the extracted plurality of events with a first set of one or more cognitive models to identify a plurality of stimulus events and a plurality of response events. Further, the method includes determining, using the first set of one or more cognitive models, an association between a first stimulus event and a first response event. The method also includes generating a stimulus-response (SR) variable for the first patient based at least in part on the determined association, and integrating the generated SR variable into one or more predictive cognitive models.

According to a second embodiment disclosed herein, a computer program product is disclosed. The computer program product comprises a computer-readable storage medium having computer-readable program code embodied therewith, the computer-readable program code executable by one or more computer processors to perform an operation. The operation comprises extracting a plurality of events from a plurality of electronic health records associated with a first patient. The operation also includes analyzing the extracted plurality of events with a first set of one or more templates to identify a plurality of stimulus events and a plurality of response events. Further, the operation includes determining, using the first set of one or more templates, an association between a first stimulus event and a first response event. The operation also includes generating a stimulus-response (SR) variable for the first patient based at least in part on the determined association, and integrating the generated SR variable into one or more predictive cognitive models.

According to a third embodiment, a system is disclosed. The system includes one or more computer processors and a memory containing a program which when executed by the one or more computer processors performs an operation. The operation comprises extracting a plurality of events from a plurality of electronic health records associated with a first patient. The operation also includes analyzing the extracted plurality of events with a first set of one or more templates to identify a plurality of stimulus events and a plurality of response events. Further, the operation includes determining, using the first set of one or more templates, an association between a first stimulus event and a first response event. The operation also includes generating a stimulus-response (SR) variable for the first patient based at least in part on the determined association, and integrating the generated SR variable into one or more predictive cognitive models.

DETAILED DESCRIPTION

Figure 1:
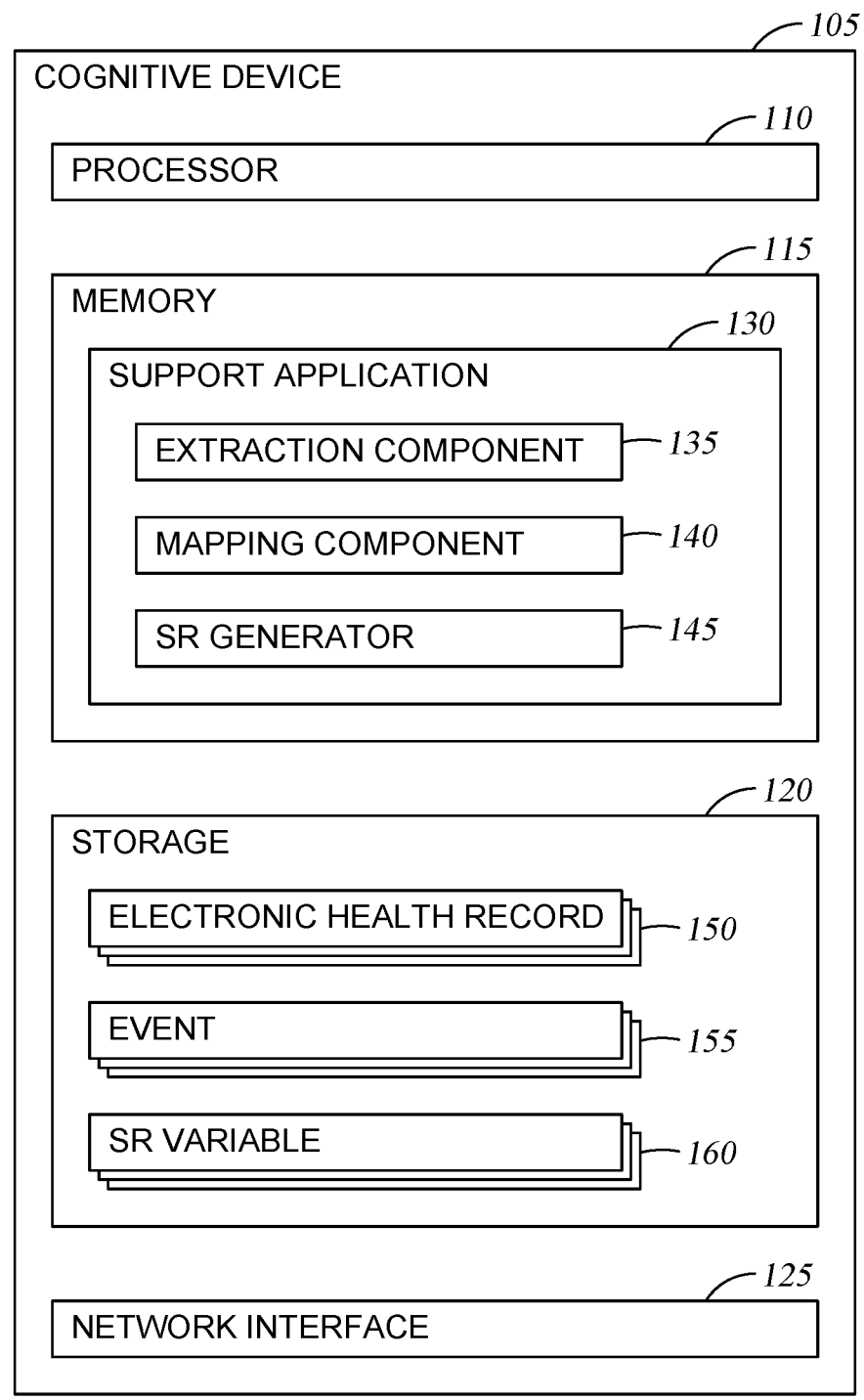
FIG. 1 is a block diagram illustrating a cognitive device for identifying and extracting stimulus-response variables, according to one embodiment disclosed herein.

Frequently, patient records are stored in electronic health records (EHR) which may include both structured and unstructured data. For example, structured data is typically organized and/or labeled (such as an "age" field in an EHR), while unstructured data is not (such as a patient's natural language description of their symptoms, or a medical professional's clinical narrative about diagnoses, treatment options, lab results, and the like). According to embodiments disclosed herein, a patient's EHR can be parsed using one or more natural language processing (NLP) techniques or models to identify and extract a wide variety of variables or covariates which may help predict patient outcomes. For example, to determine how effective a particular treatment will be or how a patient will respond to treatments, variables like whether the patient smokes, drinks alcohol, is overweight, and the like can be extracted and considered. Further, in some methodologies, more complex variables such as frequency of appointments with healthcare professionals (or trends or changes in the frequency), trends or changes in the lab measurements, and the like can also be extracted and used with various cognitive models to better predict patient outcomes. Embodiments of the present disclosure provide for the identification and extraction of behavioral covariates in the form of stimulus-response variables, which enable more accurate predictions of the way each individual patient will respond to treatments.

As used herein, variables extracted from EHR and used to predict patient outcomes may also be referred to as covariates. Further, in various embodiments, predicting patient outcomes may include forecasting whether a patient's condition will improve or decline, the magnitude of such change, the timeline of such changes (e.g., when will the improvement or decline begin, end, accelerate, and decelerate), and the like. In some embodiments, a probability is determined for each possible outcome (i.e., a probability that the patient will fully recover within a defined time period or at all, a probability that the patient will partially recover, a probability that the patient's condition will decline, and the like). Embodiments of the present disclosure may be utilized in conjunction with any disorder or malady. As used herein, a disorder refers to any medical condition, including but not limited to mental or physical disease, sickness, disability, infection, symptom, or status. In one embodiment described herein, a new type of covariate referred to as a stimulus-response (SR) variable is disclosed. In some embodiments, these SR variables may be composed of sub-data elements (such as completion status) associated with traditional data elements (such as encounter type, laboratory value, or procedure), or may be composed of multiple data elements distinguished by type and time (such as an abnormal lab value, followed by an increased number of office visits).

In embodiments, these new covariates may be used to enhance the performance of prediction models and improve analytics presented on a user interface in a clinical decision support application. In one embodiment, these SR variables serve as a measure of patient engagement and activation. Similarly, in embodiments, the SR variables may be extracted from structured or unstructured data in the patient's record, and may be extracted from multiple encounter types (e.g., online messages, telephone, in-person appointments, and the like) as well as data derived from patient portals (e.g., heart rate data uploaded by a patient to an online portal). In some embodiments, the SR variables may also depend in part on genetic data derived from genome sequencing of each patient, as well as data captured via one or more wearable sensors (including ingestible sensors).

FIG. 1 is a block diagram illustrating a Cognitive Device 105 for identifying and extracting SR Variables 160, according to one embodiment disclosed herein. As illustrated, the Cognitive Device 105 includes a Processor 110, a Memory 115, Storage 120, and a Network Interface 125. In the illustrated embodiment, Processor 110 retrieves and executes programming instructions stored in Memory 115 as well as stores and retrieves application data residing in Storage 120. Processor 110 is representative of a single CPU, multiple CPUs, a single CPU having multiple processing cores, and the like. Memory 115 is generally included to be representative of a random access memory. Storage 120 may be a disk drive or flash-based storage device, and may include fixed and/or removable storage devices, such as fixed disk drives, removable memory cards, or optical storage, network attached storage (NAS), or storage area-network (SAN). In the illustrated embodiment, the Cognitive Device 105 may be communicatively coupled with other devices through the Network Interface 125.

As illustrated, the Memory 115 includes a Support Application 130, which may be used by a healthcare provider to better predict patient outcomes. The Support Application 130 includes an Extraction Component 135, Mapping Component 140, and SR Generator 145. The illustrated Storage 120 includes one or more Electronic Health Records 150, Events 155, and SR Variables 160. In one embodiment, the Extraction Component 135 parses the Electronic Health Records 150 to identify and extract data used to generate the SR Variables 160. For example, in one embodiment, the Extraction Component 135 identifies and extracts Events 155 in the patient's data. In the context of the present disclosure, an Event 155 may refer to anything that occurs at one or more points in time in the patient's medical history. For example, in an embodiment, one Event 155 may be receiving a physician referral. Other examples of Events 155 may include (but are not limited to) completing a visit or appointment, failing to attend a visit or appointment, cancelling or rescheduling a visit or appointment, ordering or requesting health maintenance, completing or failing to complete health maintenance by a due date, ordering, requesting, or scheduling a lab measurement or a procedure, completing, rescheduling, cancelling, or missing a scheduled lab report or procedure, and the like. Similarly, in an embodiment, Events 155 may include but are not limited to receiving, recording, or providing a biometric reading or finding (e.g., blood pressure, heart rate, glucose levels, or any other biological measurement) in a health maintenance, lab report, or procedure, as well as receiving a diagnosis, opening or reviewing a lab report or other reading in person or through an online portal, and the like.

In an embodiment, the Mapping Component 140 analyzes the extracted Events 155 to identify stimulus events and response events, as well as to determine the associations or links between these events. In some embodiments, the Mapping Component 140 may also identify one or more independent events that are neither stimulus events nor response events, but merely events that occurred. As used herein, a stimulus event is an Event 155 in the patient's medical history that may trigger some sort of response by the patient. For example, receiving a medical diagnosis might be classified as a stimulus event because the patient may want to schedule a follow up visit, fill a prescription, change habits, and the like. In some embodiments, a stimulus event may be initiated or completed by the patient (e.g., recording a high blood pressure at home), or may be caused or initiated without action by the patient (e.g., receiving a diagnosis from a physician).

As used herein, a response event is an Event 155 corresponding to the patient's response to a stimulus. For example, filling a prescription (i.e., picking it up from a pharmacy) may be classified as a response event, in response to a stimulus event of receiving the prescription from a healthcare provider. In some embodiments, response events only include actions taken by the patient, such as scheduling an appointment, and do not include things that happen to the patient, such as receiving a diagnosis. Notably, in some embodiments, each response event is associated with at least one stimulus event, but a stimulus event may be associated with any number of response events, including zero. In some embodiments, the Mapping Component 140 may also identify independent events that are neither stimulus events (because they do not or would not trigger action) nor response events (because they are not caused by some other event). Additionally, in some embodiments, a single Event 155 may be identified as a stimulus event, response event, or independent event depending on various factors including the context of the Event 155. For example, an Event 155 corresponding to scheduling an appointment with a specialist may be a stimulus event (with a corresponding response event upon attending, cancelling, or rescheduling the appointment), or a response event (in response to a stimulus event corresponding to receiving a diagnosis or referral).

Further, in some embodiments, a single Event 155 may be both a stimulus event and a response event. For example, recording or uploading a blood pressure reading may be a response event in response to instructions from a doctor to periodically record blood pressure, as well as a stimulus event to schedule an appointment (for example, if the reading is abnormal or outside of the preferred range).

Additional non-limiting examples of additional stimulus-response associations may include receiving a physician referral and scheduling or completing the referral visit, having health maintenance ordered by a provider and completing or failing to complete the maintenance, ordering, requesting, or scheduling a lab or procedure and completing, rescheduling, or cancelling the lab or procedure, scheduling an appointment and completing the appointment, receiving an medical reading or diagnosis and opening or reviewing the results, recording an abnormal reading and continuing to record or upload results (at the same rate or an increased or decreased rate), and the like.

In some embodiments, stimulus-response associations may be identified between events that appear to be clinically unrelated, such as receiving a diagnosis of a first disorder, and scheduling or completing an unrelated appointment or procedure. For example, a patient may receive a diabetes diagnosis, and subsequently schedule or complete a colonoscopy. While these two events are seemingly unrelated, they may in fact constitute a stimulus-response pair because it demonstrates the patient's continuing interest in their general health, despite or perhaps because of the recent adverse diagnosis. Thus, in some embodiments, the Mapping Component 140 may identify an association between two clinically unrelated events (e.g., events that relate to different, unrelated medical disorders) based on determining that a stimulus event is the patient measuring or receiving some abnormal value or adverse result (e.g., from a procedure, diagnosis, lab test, and the like). In such an embodiment, one or more corresponding response events may be the scheduling or completion of any healthcare event (e.g., appointment, procedure, and the like). In an embodiment, this association is identified because it may indicate that the patient remains engaged and active in maintaining their health, even when they receive bad news. In some embodiments, when an adverse event occurs, the Mapping Component 140 may identify corresponding response(s) that involve preemptive or preventative care, such as scheduling a colonoscopy or check-up, when there are no apparent symptoms or maladies corresponding to the appointment. These stimulus-response pairs may be significantly predictive.

In some embodiments, a stimulus-response association can be determined within a single event in the patient data. For example, in some embodiments, an appointment, procedure, lab test, and the like may be identified in the Electronic Health Records 150, along with a corresponding status label indicating the completion status of the appointment/procedure/test. In such an embodiment, the Mapping Component 140 may identify a stimulus event of scheduling an appointment, procedure, test, and the like, and determine the response event based on the status label. For example, in one embodiment, each event may have a label such as "complete," "null," "canceled," "unknown," "deferred," "not done per patient," "not done," "declined," "patient declined," "ordered," "pending," "recommended," "erroneous," "active," and the like. If the event is a procedure and the status is "completed," the Mapping Component 140 may identify a response event indicating that the procedure was completed. Similarly, if the status indicates it was "canceled," "declined," "not done," and the like, the Mapping Component 140 may create a link indicating that the appointment was not completed. In this way, the SR Generator 145 can determine various SR Variables 160, such as the percentage of scheduled appointments that were completed, using a single identified event in the patient data and the corresponding label.

In some embodiments, if the status indicates that the appointment has not been canceled but has not yet occurred (e.g., "pending," "ordered," "recommended," "active") or that the appointment/procedure was incorrect (e.g., "erroneous"), the Mapping Component 140 may exclude this data in order to avoid using misleading values for the SR Variables 160. For example, in one embodiment, an SR Variable 160 may be defined as the number of events labeled as "completed" divided by the number of all other labels. In such an embodiment, events which are still pending should not be counted, or the corresponding SR Variable 160 will be inaccurate because events that are pending may be counted as if they were declined or canceled. Therefore, in some embodiments, these pending, ordered, recommended, active, or erroneous statuses may be excluded in order to ensure the resulting SR Variables 160 accurately reflect how many events are completed and how many are declined or canceled.

In one embodiment, once the stimulus-response associations or links have been determined, the SR Generator 145 may generate the SR Variables 160 based on these associations. For example, a first SR Variable 160 may correspond to the ratio between scheduled and completed appointments. In such an embodiment, the SR Generator 145 may identify all stimulus-response associations that match this description, and update the SR Variable 160 based on the identified associations. For example, if the patient has scheduled a total of one hundred appointments and completed ninety of them, the Mapping Component 140 may identify associated responses (i.e., completing the appointment) for ninety of the stimulus events (i.e., scheduling the appointment), and identify no corresponding response event for the remaining ten stimulus events. To continue the example, the SR Generator 145 may then determine that the corresponding SR Variable 160 has a value of ninety percent. In an embodiment, this process of may be repeated for each SR Variable 160, or for each determined association or group of Events 155. That is, the SR Generator 145 may, for each SR Variable 160, identify the corresponding Event 155 associations and update the variable, or the SR Generator 145 may, for each identified association of Events 155, determine which SR Variable 160 the group corresponds to and update the determined SR Variable 160.

In one embodiment, the type of event (i.e., stimulus, response, or independent) and the links between events are identified by the Support Application 130 based on a set of predefined rules or templates corresponding to SR Variables 160. For example, in one embodiment, a user or administrator (e.g., a healthcare provider or professional) may define a first SR Variable 160 as the ratio between scheduled appointments and completed appointments. Generally, any relationship between stimulus events and response events can be used to create an SR Variable 160. In embodiments, each SR Variable 160 generally relates to behavior or patterns of the patient, and helps to determine how the patient tends to respond to particular stimuli. In embodiments, how engaged the patient tends to be or how they tend to respond to events, as determined in the SR Variables 160, may be highly predictive of their outcomes for a planned treatment. For example, if the user tends to disengage when they receive adverse results or diagnoses (e.g., as evidenced by a low value for one or more SR Variable 160 relating to adverse or abnormal results), the patient may be less likely to keep up with more rigorous treatment options and a less demanding treatment may be preferable.

In some embodiments, one or more cognitive models may be used to define SR Variables 160 that may help predict patient outcomes. For example, one or more machine learning models may be trained based on user-defined templates or SR Variables 160, such that the models can define new SR Variables 160 for use. In one embodiment, one or more cognitive models may define an SR Variable 160, compute the value for a plurality of patients, and determine whether the defined SR Variable 160 is a good predictor for patient results based on the Electronic Health Records 150. For example, if the newly defined SR Variable 160 has a statistically significant correlation with a particular result or outcome, the system may determine that the SR Variable 160 is a useful predictor, and may parse patient data to identify and extract this data for other patients during treatment.

Figure 2:
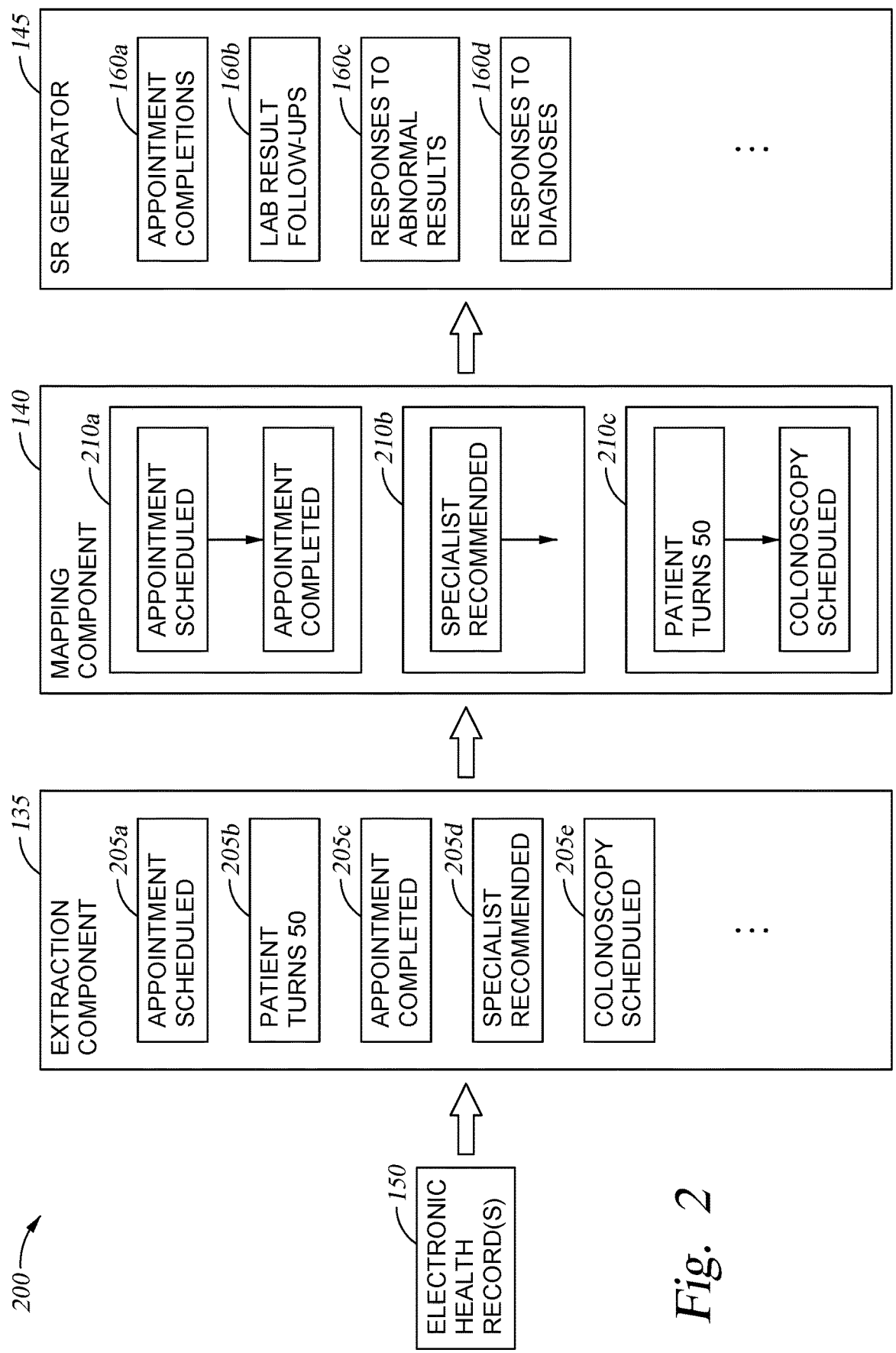
FIG. 2 illustrates a system architecture for identifying and extracting stimulus-response variables, according to one embodiment disclosed herein.

FIG. 2 illustrates a system Architecture 200 for identifying and extracting stimulus-response variables, according to one embodiment disclosed herein. As illustrated, the Extraction Component 135 ingests Electronic Health Records 150, and identifies and extracts Events 155 in the records. In an embodiment, each Electronic Health Record 150 corresponds to a particular patient that is seeking treatment. As illustrated, the Extraction Component 135 has identified several events in the patient's records. For example, as indicated by block 205*a*, an appointment with a healthcare provider was scheduled. The event represented by block 205*b* corresponds to the patient turning fifty. In block 205*c*, the patient completed an appointment. In block 205*d*, a specialist was recommended to the patient. In block 205*e*, the patient scheduled a colonoscopy. Of course, there could be any number of additional events identified. In some embodiments, Events 155 are extracted within a specified window of time. For example, in one embodiment, the Extraction Component 135 analyzes patient data from the last twelve months.

As illustrated, the Mapping Component 140 has identified a series of event associations 210*a*, 210*b*, and 210*c*. For example, in the illustrated embodiment, block 210*a* represents a first grouping where the event "appointment scheduled" has been identified as a stimulus event and "appointment completed" has been identified as the corresponding response. Although illustrated as separate events, in some embodiments, as discussed above, a single variable extracted from the Electronic Health Records 150 may encapsulate both the stimulus and response. For example, in some embodiments, the association 210*a* may have been identified based on a single "appointment" variable, with a corresponding status of "complete." As illustrated in block 210*b*, the "specialist recommended" has been identified as a stimulus event, but no corresponding response event has been identified. Finally, as illustrated in block 210*c*, the Mapping Component 140 has identified a link or association between "patient turns fifty" as a stimulus event, and "colonoscopy scheduled" as the response event. As an additional example, another response event for the stimulus 205*b* "patient turns fifty" may be "scheduled follow-up encounter." Further, as discussed above, in some embodiments, events that appear clinically unrelated (e.g., because they relate to unrelated medical concerns or disorders) may be associated by the Mapping Component 150. For example, in one embodiment, a diagnosis of diabetes may be identified as a stimulus event, with the patient scheduling a colonoscopy identified as a response event. Although these events appear entirely unrelated, they may in fact be linked by the Mapping Component 140 because they indicate an ongoing (and perhaps increased) interest in maintaining health.

After these associations and links are identified, in an embodiment, the SR Generator 145 may generate or update SR Variables 160 based on the identified events and associations. For example, as illustrated, the SR Generator 145 generates four SR Variables 160: "appointment completions" 160*a*, "lab result follow-ups" 160*b*, "responses to abnormal results" 160*c*, and "responses to diagnoses" 160*d*. Of course, in various embodiments, there may be any number of SR Variables 160 utilized. In the illustrated embodiment, the SR Generator 145 may determine that the block 210*a* corresponds to the "appointment completions" SR Variable 160*a*. Similarly, in an embodiment, the SR Generator 145 may determine that the block 210*b* should also contribute to the SR Variable 160*a*. In some embodiments, block 210*b* may instead be related to one or more other SR Variables 160, such as a "specialist referral rate" variable. In one embodiment, because no corresponding response variable was found for block 210*b*, the SR Generator 145 may count this as a missed or cancelled appointment, which would reduce the value of the SR Variable 160*a*.

In some embodiments, however, the SR Generator 145 may determine that the response is still pending, and exclude this data from the SR Variables 160. For example, in one embodiment, the specialist referral event may have a status indicating that it is scheduled or pending. In some embodiments, the "specialist recommended" event may be associated with a deadline or due date, and the SR Generator 145 may exclude the data if this deadline has not yet been reached. In some embodiments, the SR Generator 145 may create a deadline for events which do not have a labeled deadline, based on a predefined period of time. For example, in one embodiment, appointments may be considered "pending" unless the deadline has passed, they are labeled "canceled" or an equivalent, or a predefined period of time has passed.

In the illustrated embodiment, the SR Generator 145 may further determine that the block 210*c* corresponds to the SR Variable 160*c* relating to how the patient responds to abnormal or adverse results from testing. For example, this variable may include information relating to whether the patient becomes disengaged from healthcare items (such as appointments, regular testing, and the like), becomes more engaged (initiating extra testing, uploading more results, etc.) or remains the same. As illustrated, the scheduling of a colonoscopy is identified as a response to the abnormal reading, which may indicate that the patient will remain engaged (and perhaps increase attention to healthcare issues) when they receive abnormal results. Of course, these SR Variables 160 are merely included as examples, and many other stimulus-response pairings and SR Variables 160 may be identified in various embodiments.

In some embodiments, one or more of the SR Variables 160 include numerical data. For example, the SR Variable 160*a* may include a percentage of appointments that are completed on schedule. Similarly, the SR Variable 160*b* may include a ratio between the number of lab results received, and the number of times the patient followed up with a physician to discuss the results (via an online portal, email, telephone, in person, and the like). Additionally, the SR Variable 160*c* may include information relating to patient engagement after adverse results, such as whether it increases or decreases, and the magnitude of the change. Additionally, the SR Variable 160*d* may similarly indicate (e.g., via a vector with both direction and magnitude) how the patient responds to receiving a diagnosis. In some embodiments, the value of one or more SR Variables 160 may also be based at least in part on the time that elapsed between the stimulus and response. For example, if a patient scheduled a follow-up within a week of receiving an adverse diagnosis, the associated SR Variable 160 may have a different value than if the patient waited a month to schedule the follow-up, even though they still eventually followed-up.

Figure 3:
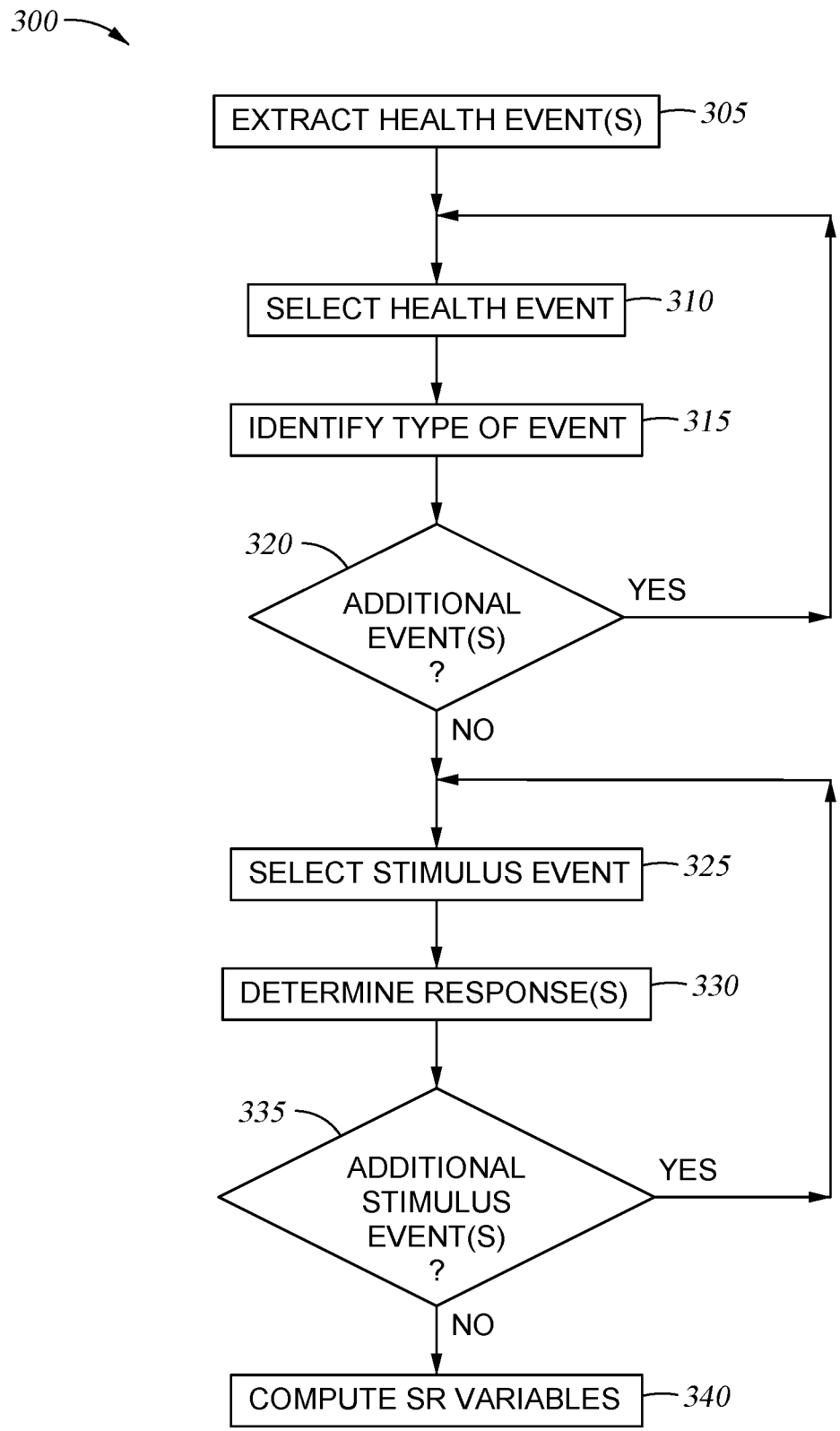
FIG. 3 is a flow diagram illustrating a method of identifying and extracting stimulus-response variables, according to one embodiment disclosed herein.

FIG. 3 is a flow diagram illustrating a method 300 of identifying and extracting stimulus-response variables, according to one embodiment disclosed herein. The method 300 begins at block 305, where the Extraction Component 135 identifies and extracts health events from the Electronic Health Records 150 using one or more cognitive models and/or NLP techniques. At block 310, the Mapping Component 140 selects a first identified health event, and at block 315, the Mapping Component 140 identifies the type of the event. For example, as discussed above, in one embodiment, an event may be a stimulus event, response event, both, or neither. The method 300 then proceeds to block 320, where it is determined whether additional events remain to be processed. If so, the method 300 returns to block 310 to select the next event. Otherwise, the method 300 continues to block 325.

At block 325, the Mapping Component 140 selects one of the identified stimulus events. The method 300 proceeds to block 330, where the Mapping Component 140 determines the corresponding response(s) by identifying any response events that correspond to the selected stimulus event. As discussed above, in some embodiments, this determination is based on one or more templates or rules. In some embodiments, this determination may be made by one or more cognitive models or machine learning models. In some embodiments, the response event may be determined based on a status label associated with the stimulus event, as discussed above. In some embodiments, a single stimulus event may include multiple response events. Additionally, in some embodiments, a stimulus event may not have any corresponding response events. This may be, for example, because the patient has not yet responded to the stimulus (e.g., because insufficient time has passed, or because the patient is not going to respond to the stimulus). The method 300 then proceeds to block 335, where it is determined whether there are additional stimulus events that have not yet been processed. If so, the method 300 returns to block 325. If not, the method 300 proceeds to block 340, where the SR Generator 145 generates one or more SR Variables 160 based on the determined associations. For example, as discussed above, associations related to how often the patient completes scheduled events such as appointments may correspond to a first SR Variable 160, while how often the patient completes scheduled procedures may correspond to a second SR Variable 160.

In some embodiments, once the SR Variables 160 are computed, the Support Application 130 may integrate them into one or more predictive cognitive models used to determine patient outcomes. In an embodiment, a cognitive model can analyze longitudinal data to identify points in time in which a physician can provide decisions regarding a patient's disorder. For instance, the model can identify all office encounters associated with abnormal blood pressure values for a population of patients suffering from hypertension. In an embodiment, the model can then extract a large collection of covariates, including traditional ones as well as SR covariates discussed herein. Further, the model may identify an outcome for each patient in the population (e.g., a binary outcome: blood pressure either is under control or abnormal within a given follow-up window, or a complex outcome: set of new symptoms, with associated weights). In one embodiment, the cognitive model then uses a machine learning algorithm to identify the most informative covariates capable of predicting the outcome. When a future patient is seen by the physician, that patient's covariates (including his or her SR variables) are used to query the model (represented by a data structure that combines associations between past patients, covariates, and outcomes), and help the physician to choose the potentially most efficient treatment.

For example, in one embodiment, one or more cognitive models may be trained to predict patient results based on a number of covariates like smoking status, age, cholesterol levels, glucose levels, and the like. In an embodiment, these cognitive models can be further refined using one or more SR Variables 160 to create more accurate prediction models. For example, the patient's appointment completion rate may indicate how likely they are to keep up with treatments and appointments in the future, which may influence which treatment plan is selected. For example, a treatment plan requiring frequent check-ins with a physician may be ill-suited for a patient with a history of missing appointments, which will lead to a lower probability that the disorder will be managed if this treatment plan is selected.

Figure 4:
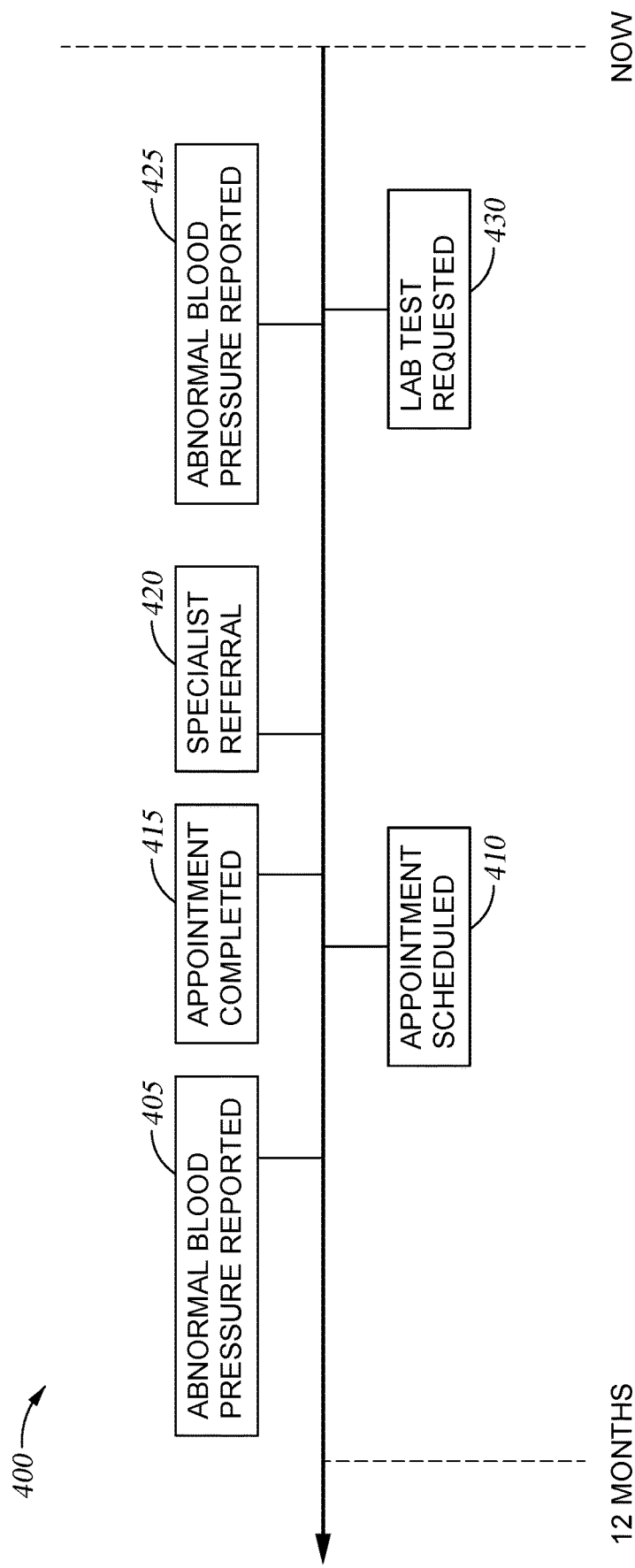
FIG. 4 illustrates a timeline of healthcare events that can be parsed to identify and extract stimulus-response variables, according to one embodiment disclosed herein.

FIG. 4 illustrates a timeline 400 of healthcare events that can be parsed to identify and extract stimulus-response variables, according to one embodiment disclosed herein. In the illustrated embodiment, the present time is located on the right side of the timeline 400, and events further to the left are further back in time. As illustrated, the timeline extends twelve months into the past. That is, in the illustrated embodiment, only events or variables from the last twelve months are considered when generating the SR Variables 160. As illustrated, the Extraction Component 135 has identified six events corresponding to blocks 405, 410, 415, 420, 425, and 430. At block 405, the patient's health records indicate that an abnormal blood pressure was reported. This may have been reported by the patient, recorded by a healthcare provider, and the like. At block 410, the patient scheduled an appointment with a care provider. At block 415, the patient completed the scheduled appointment. At block 420, the patient received a specialist referral. At block 425, a second abnormal blood pressure was reported, and at block 430, a lab test was requested.

In the illustrated embodiment, the Matching Component 140 may identify a number of stimulus and response events, as well as associations or links between them, depending on the particular methods used and the defined SR Variables 160. For example, in one embodiment, the Matching Component 140 may determine that block 410, scheduling an appointment, was a response to block 405, where abnormal blood pressure was reported. Further, the Matching Component 140 may identify block 415 as a response to the stimulus of block 410. In this way, block 410 may act as both a stimulus and a response. Further, the Matching Component 140 may determine that block 420 is a stimulus event because it would typically cause a subsequent response. However, no subsequent response is available (i.e., the patient has not followed up on the referral). In one embodiment, the Matching Component 140, the may identify block 425 as a stimulus event, because it may cause the patient to seek additional treatments. In some embodiments, the Matching Component 140 may also identify block 425 as a response event. For example, the patient may have checked their blood pressure again in response to the prior high reading, in response to the appointment, in response to the specialist referral, or in response to a combination of events. Similarly, the block 430 may be classified as a response event if the patient requested the test, or as another stimulus event if it was recommended by a physician. Of course, the above classifications will depend on the particular models utilized, and the particular definitions of SR Variables 160 used in the system.

Figure 5:
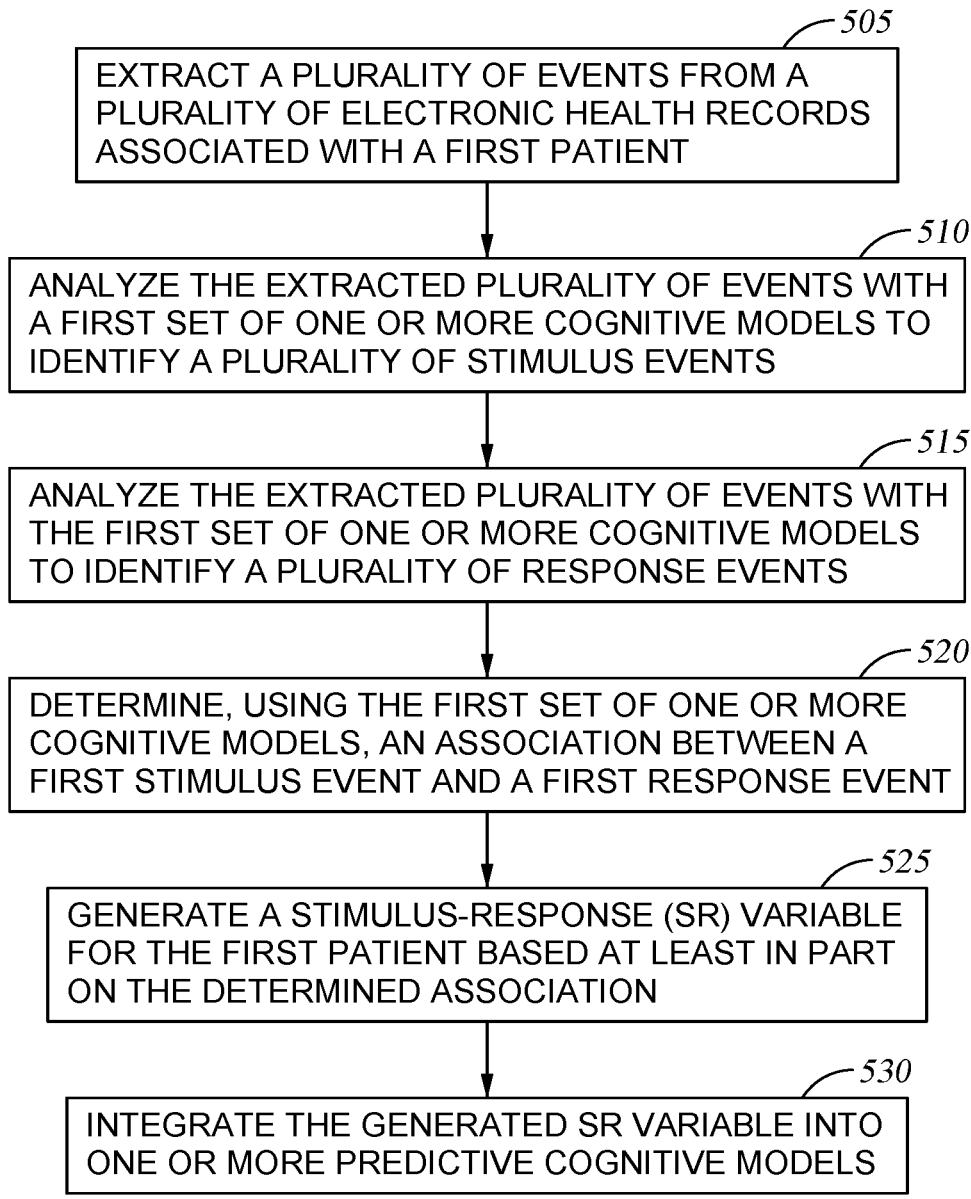
FIG. 5 is a flow diagram illustrating a method of identifying and extracting stimulus-response variables, according to one embodiment disclosed herein.

FIG. 5 is a flow diagram illustrating a method 500 of identifying and extracting stimulus-response variables, according to one embodiment disclosed herein. The method 500 begins at block 505, where the Support Application 130 extracts a plurality of events from a plurality of electronic health records associated with a first patient. At block 510, the Support Application 130 analyzes the extracted plurality of events with a first set of one or more cognitive models to identify a plurality of stimulus events. As discussed above, in some embodiments, the Support Application 130 may utilize one or more rules-based templates to identify stimulus events. In embodiments, any suitable method of identifying and extracting stimulus and response variables may be utilized. The method 500 continues to block 515, where the Support Application 130 analyzes the extracted plurality of events with the first set of one or more cognitive models to identify a plurality of response events. Similarly, as discussed above, in some embodiments, the Support Application 130 may utilize one or more rules-based templates to identify response events. Further, at block 520, the Support Application 130 determines, using a second set of one or more cognitive models, an association between a first stimulus event and a first response event. Similarly, as discussed above, in some embodiments, the Support Application 130 may utilize one or more rules-based templates to determine the associations between events. The method 500 then proceeds to block 525, where the Support Application 130 generates a stimulus-response (SR) variable for the first patient based at least in part on the determined association. Finally, the method 500 concludes at block 530, where the Support Application 130 integrates the generated SR variable into one or more predictive cognitive models.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., Support Application 130) or related data available in the cloud. For example, the Support Application 130 could execute on a computing system in the cloud and identify and extract SR Variables 160. In such a case, the Support Application 130 could parse Electronic Health Records 150 and store generated SR Variables 160 at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
training a first set of one or more machine learning models, based on one or more stimulus-response (SR) variables defined by a user, to define new SR variables;
defining a new SR variable using the trained first set of one or more machine learning models, wherein the new SR variable indicates whether patient engagement increases in response to adverse events;
determining, for each respective patient of a plurality of patients, a respective value of the new SR variable;
validating the new SR variable by determining, based on the respective values of the new SR variable, that the new SR variable has a statistically significant correlation with a defined patient outcome;
extracting a plurality of events from a plurality of electronic health records associated with a first patient, wherein the plurality of electronic health records correspond to a defined period of time;
analyzing the extracted plurality of events using the trained first set of one or more machine learning models to identify a plurality of stimulus events and a plurality of response events, wherein only the plurality of electronic health records corresponding to the defined window of time are analyzed, comprising:
classifying a first event of the extracted plurality of events as a first stimulus event, based at least in part on determining that the first event corresponds to new information received by the first patient, wherein the new information relates to a first medical disorder, classifying a second event of the extracted plurality of events as a first response event, based at least in part on determining that the second event corresponds to an action taken by the first patient, wherein the action is clinically unrelated to the first medical disorder, classifying a third event of the extracted plurality of events as a second stimulus event, and excluding the second stimulus event from the extracted plurality of events, based on determining that a deadline associated with the second stimulus event has not passed;

determining, using the trained first set of one or more machine learning models, a link between the first stimulus event and the first response event, based on determining that the first patient took the action in response to receiving the new information, wherein the action is clinically unrelated to the new information;

generating a value for the new SR variable with respect to the first patient based at least in part on the determined association, wherein the value for the new SR variable indicates a ratio between a number of healthcare appointments scheduled for the first patient and a number of healthcare appointments completed by the first patient corresponding to the defined period of time, and a time elapsed between the first stimulus event and the first response event; and in response to validating the new SR variable, training one or more predictive machine learning models to predict patient outcomes using the new SR variable, based at least in part on the generated value for the new SR variable with respect to the first patient.

2. The method of claim 1, wherein the first event of the plurality of events corresponds to a laboratory measurement, wherein a corresponding value of the laboratory measurement is also extracted from the plurality of electronic health records.

3. The method of claim 2, wherein the corresponding value of the laboratory measurement is outside of a normal range, and wherein the first event is identified as the first stimulus event.

4. The method of claim 3, wherein the second event of the plurality of events corresponds to scheduling a healthcare appointment, wherein the second event is identified as the first response event.

5. The method of claim 1, wherein at least one event of the plurality of events corresponds to a medical procedure or healthcare appointment being scheduled, completed, or cancelled.

6. The method of claim 1, wherein the first stimulus event corresponds to receiving a laboratory measurement relating to a first disorder, and the first response event corresponds to scheduling a healthcare appointment for a second disorder, wherein the first and second disorders are unrelated.

7. The method of claim 1, wherein the SR variable indicates a ratio between a number of procedures completed and a number of procedures scheduled.

8. The method of claim 1, the method further comprising:
identifying a proposed healthcare plan; and
using the one or more predictive machine learning models to determine a probable outcome of the proposed healthcare plan, comprising, generating a respective probability for each respective outcome of a plurality of possible outcomes, wherein the plurality of possible outcomes comprise:

full recovery of a patient within a defined period of time;
partial recovery of a patient; and
a decline in condition of a patient.

9. A computer program product comprising a computer-readable storage medium having computer-readable program code embodied therewith, the computer-readable program code executable by one or more computer processors to perform an operation comprising:

training a first set of one or more machine learning models, based on one or more stimulus-response (SR) variables defined by a user, to define new SR variables;

defining a new SR variable using the trained first set of one or more machine learning models, wherein the new SR variable indicates whether patient engagement increases in response to adverse events;

determining, for each respective patient of a plurality of patients, a respective value of the new SR variable;

validating the new SR variable by determining, based on the respective values of the new SR variable, that the new SR variable has a statistically significant correlation with a defined patient outcome;

extracting a plurality of events from a plurality of electronic health records associated with a first patient, wherein the plurality of electronic health records correspond to a defined period of time;

analyzing the extracted plurality of events using the trained first set of one or more machine learning models to identify a plurality of stimulus events and a plurality of response events, wherein only the plurality of electronic health records corresponding to the defined window of time are analyzed, comprising:

classifying a first event of the extracted plurality of events as a first stimulus event, based at least in part on determining that the first event corresponds to new information received by the first patient, wherein the new information relates to a first medical disorder, classifying a second event of the extracted plurality of events as a first response event, based at least in part on determining that the second event corresponds to an action taken by the first patient, wherein the action is clinically unrelated to the first medical disorder, classifying a third event of the extracted plurality of events as a second stimulus event, and excluding the second stimulus event from the extracted plurality of events, based on determining that a deadline associated with the second stimulus event has not passed;

determining, using the trained first set of one or more machine learning models, a link between the first stimulus event and the first response event, based on determining that the first patient took the action in response to receiving the new information, wherein the action is clinically unrelated to the new information;

generating a value for the new SR variable with respect to the first patient based at least in part on the determined association, wherein the value for the new SR variable indicates a ratio between a number of healthcare appointments scheduled for the first patient and a number of healthcare appointments completed by the first patient corresponding to the defined period of time, and a time elapsed between the first stimulus event and the first response event; and in response to validating the new SR variable, training a predictive machine learning model to predict patient outcomes using the new SR variable, based at least in part on the generated value for the new SR variable with respect to the first patient.

10. The computer program product of claim 9, wherein at least one event of the plurality of events corresponds to a medical procedure or healthcare appointment being scheduled, completed, or cancelled.

11. The computer program product of claim 9, wherein the first stimulus event corresponds to receiving a laboratory measurement relating to a first disorder, and the first response event corresponds to scheduling a healthcare appointment for a second disorder, wherein the first and second disorders are unrelated.

12. The computer program product of claim 9, wherein the SR variable indicates a ratio between a number of procedures completed and a number of procedures scheduled.

13. The computer program product of claim 9, the operation further comprising:
identifying a proposed healthcare plan; and
using the one or more predictive machine learning models to determine a probable outcome of the proposed healthcare plan, comprising, generating a respective probability for each respective outcome of a plurality of possible outcomes, wherein the plurality of possible outcomes comprise:
full recovery of a patient within a defined period of time;
partial recovery of a patient; and
a decline in condition of a patient.

14. A system comprising:
one or more computer processors; and
a memory containing a program which when executed by the one or more computer processors performs an operation, the operation comprising:
training a first set of one or more machine learning models, based on one or more stimulus-response (SR) variables defined by a user, to define new SR variables;
defining a new SR variable using the trained first set of one or more machine learning models, wherein the new SR variable indicates whether patient engagement increases in response to adverse events;
determining, for each respective patient of a plurality of patients, a respective value of the new SR variable;
validating the new SR variable by determining, based on the respective values of the new SR variable, that the new SR variable has a statistically significant correlation with a defined patient outcome;
extracting a plurality of events from a plurality of electronic health records associated with a first patient, wherein the plurality of electronic health records correspond to a defined period of time;
analyzing the extracted plurality of events using the trained first set of one or more machine learning models to identify a plurality of stimulus events and a plurality of response events, wherein only the plurality of electronic health records corresponding to the defined window of time are analyzed, comprising:
classifying a first event of the extracted plurality of events as a first stimulus event, based at least in part on determining that the first event corresponds to new information received by the first patient, wherein the new information relates to a first medical disorder,
classifying a second event of the extracted plurality of events as a first response event, based at least in part on determining that the second event corresponds to an action taken by the first patient, wherein the action is clinically unrelated to the first medical disorder,
classifying a third event of the extracted plurality of events as a second stimulus event, and
excluding the second stimulus event from the extracted plurality of events, based on determining that a deadline associated with the second stimulus event has not passed;
determining, using the trained first set of one or more machine learning models, a link between the first stimulus event and the first response event, based on determining that the first patient took the action in response to receiving the new information, wherein the action is clinically unrelated to the new information;
generating a value for the new SR variable with respect to the first patient based at least in part on the determined association, wherein the value for the new SR variable indicates a ratio between a number of healthcare appointments scheduled for the first patient and a number of healthcare appointments completed by the first patient corresponding to the defined period of time, and a time elapsed between the first stimulus event and the first response event; and
in response to validating the new SR variable, training one or more predictive machine learning models to predict patient outcomes using the new SR variable, based at least in part on the generated value for the new SR variable with respect to the first patient.

15. The system of claim 14, wherein at least one event of the plurality of events corresponds to a medical procedure or healthcare appointment being scheduled, completed, or cancelled.

16. The system of claim 14, wherein the first stimulus event corresponds to receiving a laboratory measurement relating to a first disorder, and the first response event corresponds to scheduling a healthcare appointment for a second disorder, wherein the first and second disorders are unrelated.

17. The system of claim 14, the operation further comprising:
identifying a proposed healthcare plan; and
using the one or more predictive machine learning models to determine a probable outcome of the proposed healthcare plan, comprising, generating a respective probability for each respective outcome of a plurality of possible outcomes, wherein the plurality of possible outcomes comprise:
full recovery of a patient within a defined period of time;
partial recovery of a patient; and
a decline in condition of a patient.

* * * * *